United States Patent [19]

Kenna

[11] Patent Number: 5,151,104
[45] Date of Patent: Sep. 29, 1992

[54] SELF-LOCKING JOINT CONNECTOR

[75] Inventor: Robert V. Kenna, Hobe Sound, Fla.

[73] Assignee: Pfizer Hospital Products Group, Inc., New York, N.Y.

[21] Appl. No.: 427,652

[22] Filed: Oct. 26, 1989

[51] Int. Cl.⁵ .............................................. A61B 17/56
[52] U.S. Cl. ........................................ 606/73; 623/13
[58] Field of Search ....................... 606/72, 73, 60, 65; 623/13, 14, 18, 20

[56] References Cited

U.S. PATENT DOCUMENTS

| 4,301,551 | 11/1981 | Dore et al. | 623/13 |
|---|---|---|---|
| 4,628,923 | 12/1986 | Medoff | 606/65 |
| 4,640,271 | 2/1987 | Lower | 606/65 |
| 4,744,793 | 5/1988 | Parr et al. | 623/13 |
| 4,755,183 | 7/1988 | Kenna | 623/13 |
| 4,828,562 | 5/1989 | Kenna | 623/13 |
| 4,870,957 | 10/1989 | Goble et al. | 623/13 X |

FOREIGN PATENT DOCUMENTS

| 232049 | 8/1987 | European Pat. Off. | 623/13 |
|---|---|---|---|
| 3710587 | 10/1988 | Fed. Rep. of Germany | 623/13 |
| 2039220 | 8/1980 | United Kingdom | 623/13 |

Primary Examiner—Robert A. Hafer
Assistant Examiner—Kevin G. Rooney
Attorney, Agent, or Firm—Peter C. Richardson; Lawrence C. Akers; Elizabeth O. Slade

[57] ABSTRACT

A device suitable for use in a wide variety of types of joints of the body of a human or other mammal is provided. The device is especially useful for implantation into the human femur so as to repair an anterior cruciate ligament. The device is self-locking and can be used to connect two parts of a joint together by means of an artificial ligament (if desired) or by means of a biological graft (either allegraft or autogenous, including bone with a natural tendon attached thereto). The device permits the surgeon very simply to do a revision from such a mechanical ligament to a biological graft or vice-versa, as desired; that is, the device of the invention is fully revisable. A method of connecting two parts of a joint is also given.

8 Claims, 6 Drawing Sheets

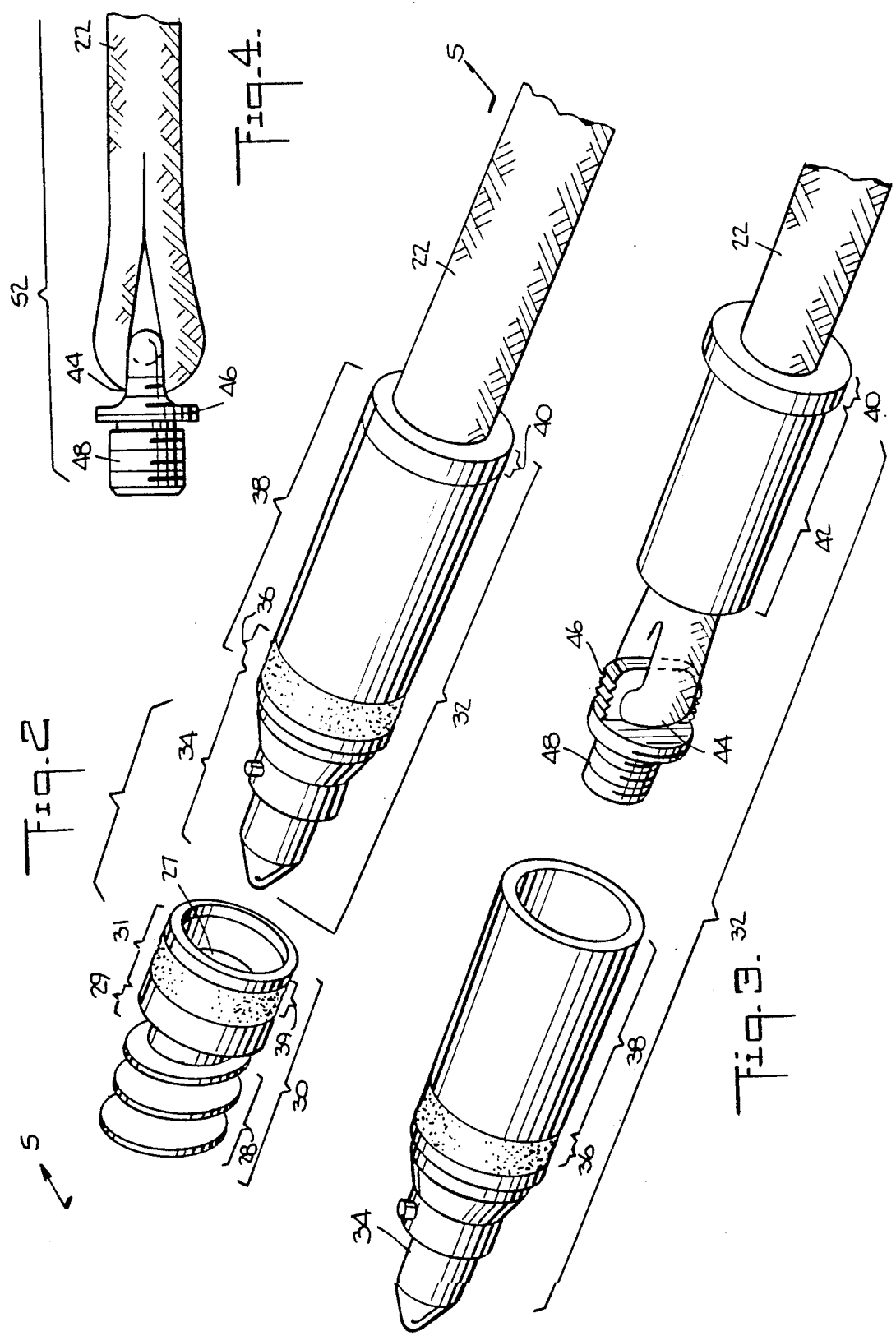

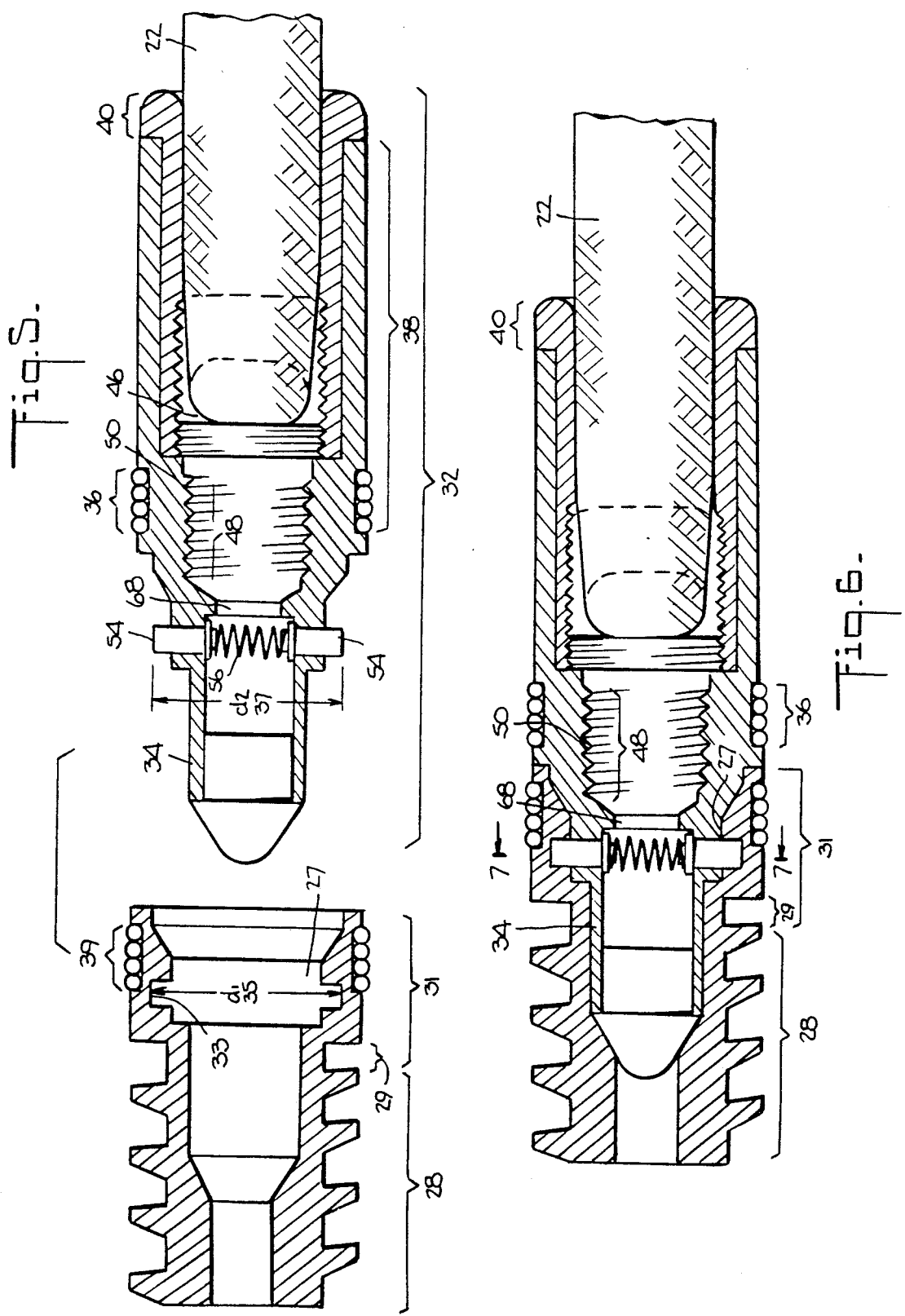

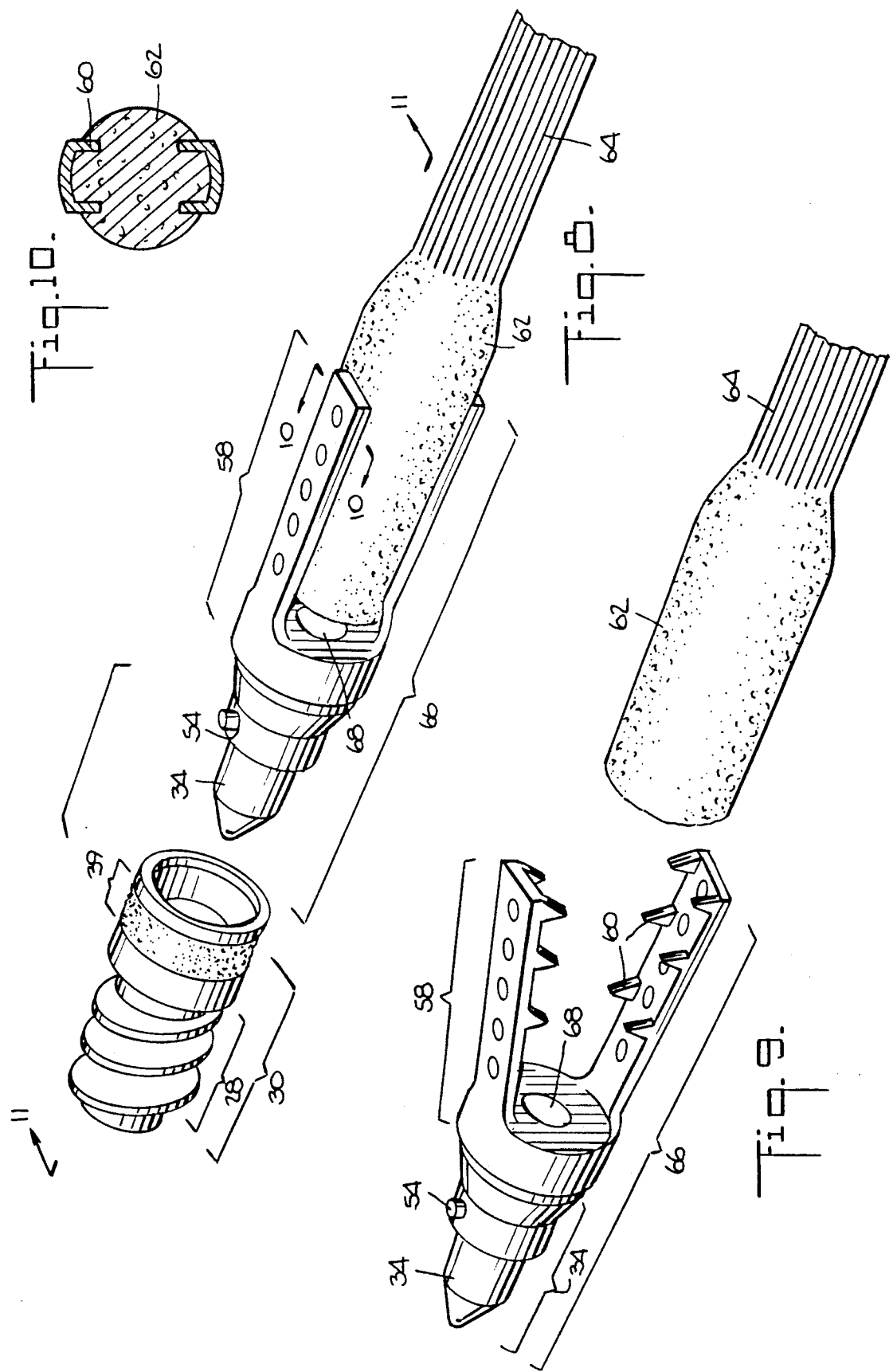

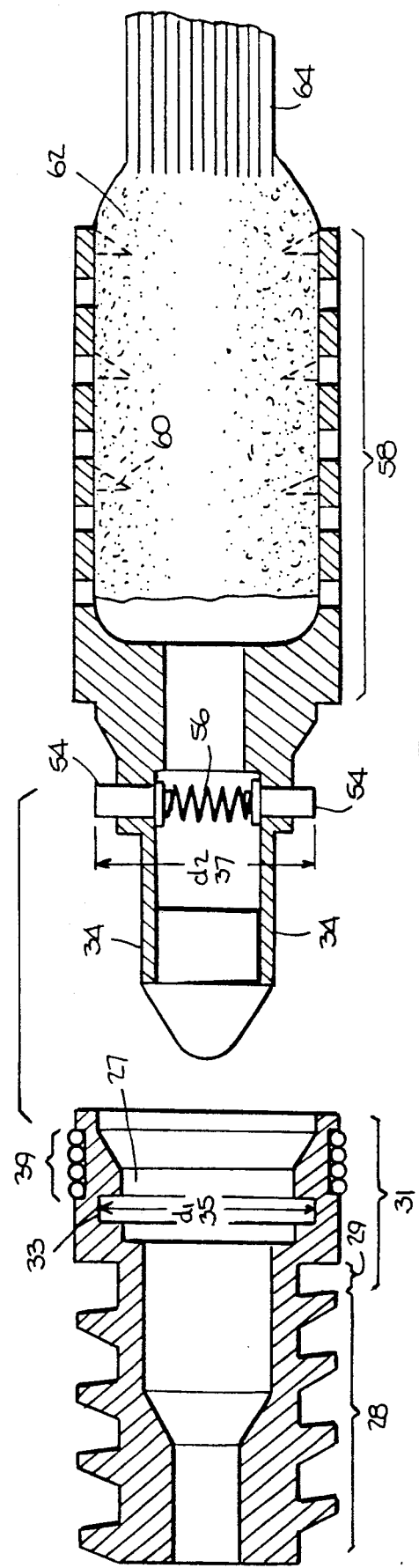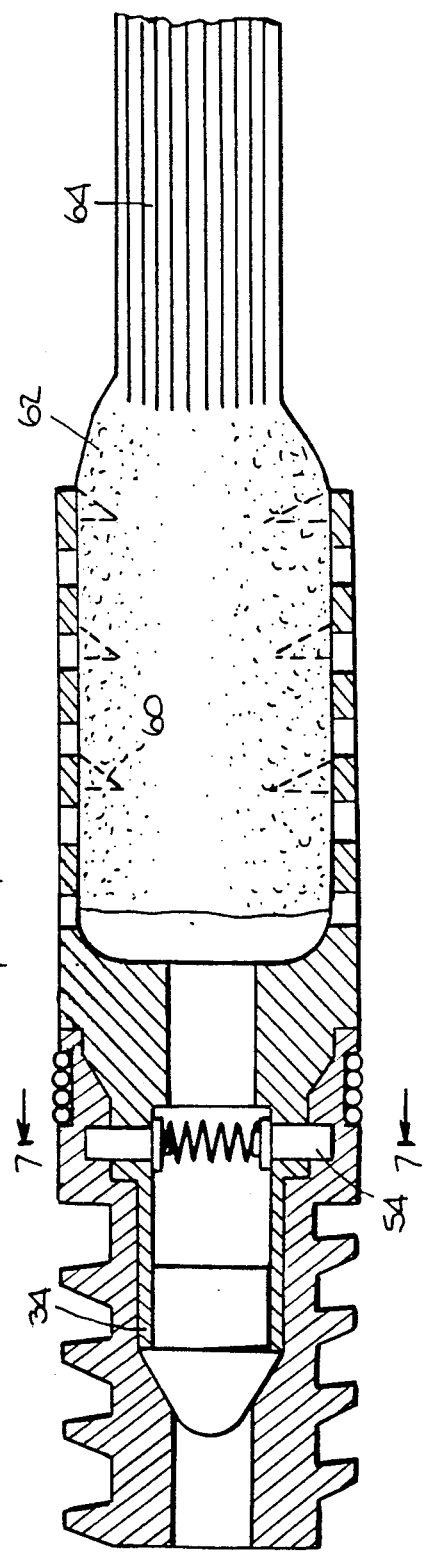

SELF-LOCKING JOINT CONNECTOR

BACKGROUND OF THE INVENTION

In the prior art, many fixation devices have been invented for use in repairing joints which have been injured. One very useful device is described and claimed in U.S. Pat. No. 4,828,562, and that patent is hereby incorporated herein by reference. One use of that fixation device is for repairing an anterior cruciate ligament.

In all known prior art fixation devices for repairing joints in bodies of humans and in other mammals, the devices are such that at least a part of the device goes through the lateral cortex and into muscle. Such implantation is undesirable because the soft tissue will atrophy and die in the area where it contacts such a device. Therefore, there has been a continuing need for a device for fixing parts of a joint which does not go through the lateral cortex and into muscle. An object of this invention is such a fixation device.

A further object of the invention is a device which, once it has been implanted, is securely locked into place. A further object of this invention is a device which is suitable for being implanted very easily into a patient (i.e., a self-locating device) and which is suitable for being revised from having a mechanical (or artificial) ligament attached thereto to having a bone graft-natural tendon (either allegraft or autogenous) attached thereto or vice-versa.

SUMMARY OF THE INVENTION

These and other objects are satisfied by the device according to the invention which comprises a self-locking device suitable for connecting two parts of a joint together.

The device in one embodiment preferably includes a portion having a screw at one end thereof (which is to be screwed into bone) and has also connected to that screw portion a cylindrical portion with a locking means (for example, a groove) located therein. The device includes also a separate second portion which has a locking means (for example, two spring-loaded collapsible pins) located therein which is adapted to lock into and remain self-locked with the locking means in the cylindrical portion.

The device according to the invention is especially useful for having the screw portion thereof be inserted into the femur (preferably into the intercondular notch) and having either a mechanical (i.e., synthetic) ligament or a bone graft-natural tendon (either allegraft or autogenous) be connected to the end of the second portion of the device (at its end opposite the locking means). The device is especially suitable for use with any other device in which the tension of the ligament can be adjusted. The device can be used in a wide variety of types of joints.

Also according to the invention, a method of repairing a joint of a mammal includes drilling a hole into bone in one side of the joint, placing the screw of the first portion of the device of the invention into the drilled hole; and then inserting into the first portion either (1) the mechanical ligament device embodiment of the second portion of the device of the invention (to which an artificial ligament is attached) or alternatively (2) the embodiment of the second portion of the device of the invention which has teeth which are attachable to a bone graft with a natural tendon (either allegraft or autogenous) attached thereto, so that the first and second portion are locked together.

DESCRIPTION OF THE PREFERRED EMBODIMENTS

Brief Description of the Drawings

FIG. 2 is an exploded view of the embodiment of the invention shown in FIG. 1, but with the first component of the device being separated from the second component of the device.

FIG. 3 is an exploded view of the embodiment of the second portion of the device shown in FIG. 2, showing the main housing body of the nose portion of the device and the end portion having a replaceable ligament woven around a loop, the end portion being screwed at one end into the nose body and having a protective cover with a highly polished internal diameter for preventing abrasion of the artificial ligament.

FIG. 4 is a pictorial representation of the woven ligament shown in FIG. 3 which is woven around a loop, but rotated through an angle of 90°, the loop and the woven ligament forming a part which is replaceable.

FIG. 5 is a view in cross-section taken along the lines 5—5 in FIG. 2.

FIG. 6 is a view in cross-section showing the parts which were separated in FIG. 5 in their interlocked position, the locking mechanism comprising (in a preferred embodiment) spring-loaded collapsible pins in the nose portion of the device snapped into place in a groove in the first portion of the device.

FIG. 8 is a pictorial view of the first portion of the device (which has a screw at one end thereof and a groove located within and near the other end thereof), shown separated from a second embodiment of the second portion of the device wherein this second embodiment has affixed thereto a bone plug with a natural tendon (the bone graft-tendon being either allegraft or autogenous) attached thereto.

FIG. 9 is an exploded view, showing the bone graft-tendon of FIG. 8 before it has been inserted within the embodiment of the second portion of the device shown in FIG. 8, showing the teeth which are to be embedded into bone when the device is attached to the bone.

FIG. 10 is a view in cross-section taken along the lines 10—10 in FIG. 8 in the direction of the arrows.

FIG. 11 is a view in cross-section, taken along the lines 11—11 in the direction of the arrows shown in FIG. 8, with the first portion of the device of the invention shown separated from the second embodiment of the second portion of the device of the invention.

FIG. 12 is a view in cross-section of the embodiment of the invention which was shown in FIG. 11 but shown in its self-locked position, with two spring-loaded collapsible pins snapped into a groove in the first portion of the embodiment of the device of the invention shown in FIG. 11.

DETAILED DESCRIPTION OF THE DRAWINGS

Figure 1:
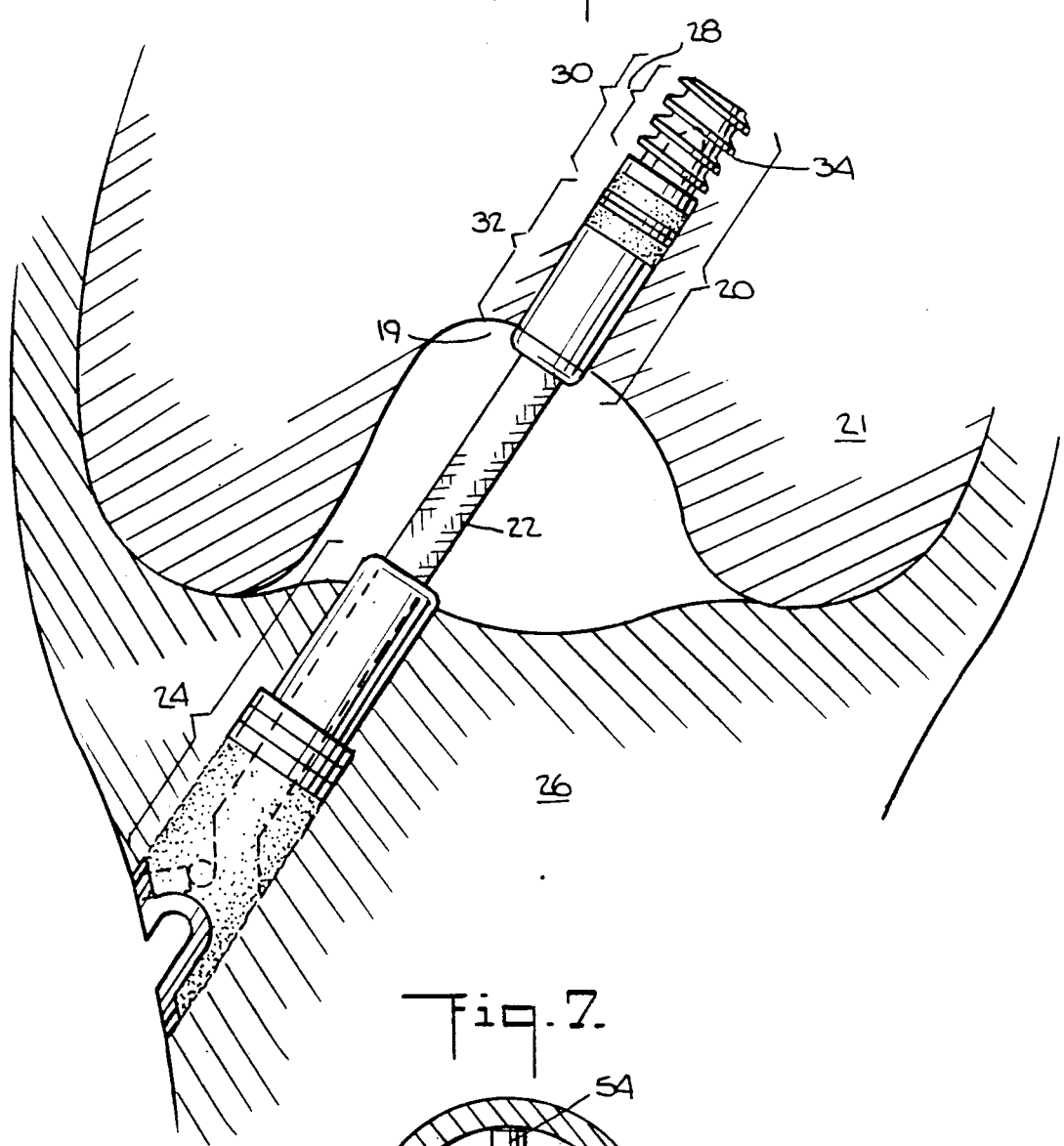
FIG. 1 is a pictorial representation of an embodiment of the device according to the invention which is especially useful for repairing an anterior cruciate ligament, with the first portion of the device shown embedded within a porthole (labeled X) in the intercondular notch in the femur side of the knee joint, such that a cavity (i.e., a blind hole) rather than a tunnel is present and the screw is screwed within that blind hole, so as to position that embodiment of the device of the invention. Substantially the entire housing is implanted into the bone, with a small portion (i.e., about 1 mm.) of the device extending above the surface of the bone such that if any bending of ligament 22 occurs, ligament 22 will not touch the surface of the bone. An artificial ligament is shown connected at one of its ends to an embodiment of the second portion of the device of the invention (i.e., a mechanical ligament device) and is connected at its other end to a fixation device as was disclosed and claimed in U.S. Pat. No. 4,828,562, which is useful for adjusting the tension of the artificial ligament.
Figure 7:
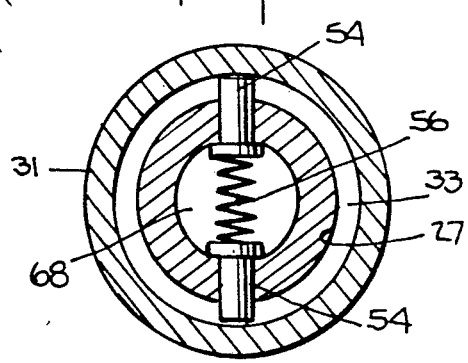
FIG. 7 is a view in cross-section taken along the lines 7—7 of FIG. 6, showing the locking mechanism which in a preferred embodiment comprises self-locking collapsible pins and an internal spring which provides the spring-loading).

In FIG. 1, a first embodiment referred to generally as 20 of the device of the invention is shown positioned within the femur side 21 of the knee joint of the body, located within a porthole in the intercondular notch 19 (labeled with an X). The porthole makes a cavity or blind hole, rather than a tunnel passing all of the way through the bone). An artificial ligament 22 is shown connected to first embodiment 20 of the invention at one of its ends; and at its other end, artificial ligament 22 is shown connected to a device 24 which is fully disclosed and claimed in U.S. Pat. No. 4,828,562 (which is suitable for adjusting the tension of the artificial ligament 22, and which is positioned on the tibial 26 side of the femur-tibial joint).

The first embodiment 20 of the device of the invention, as shown in FIG. 1, has a first portion 30 (which also is used in the second embodiment, described below and shown in detail in FIGS. 8-12). That is, in the first embodiment of the invention (shown and described in FIGS. 1-6), the first portion 30 of that embodiment of the device of the invention is identical to the first portion 30 of the second embodiment of the invention (shown in FIGS. 8-12).

Also shown in FIG. 1 is a second portion 32, which has a nose portion 34 (shown in dotted lines in FIG. 1), which extends into first portion 30 and which is shown in FIG. 1 in its locked position as it would be positioned after it has been implanted into the body.

In FIG. 2, the embodiment of the device of the invention which was shown assembled in FIG. 1 is shown with its component parts separated. In FIG. 2, first portion 30 is shown in detail with its component parts, including screw portion 28, connecting portion 29, and end portion 31 having a bore 27 (and having a groove 33 located therein, not shown in FIG. 2 but described below). Second portion 32 of the first embodiment is shown in FIG. 2, with its component parts, including nose portion 34, mid-section 36 (which can if desired, be porous coated), and main housing body 38 (which is integrally connected to mid-section 36). If desired, end portion 31 can have a portion 39 thereof be porous coated.

In FIG. 3, second portion 32 of the first embodiment of the invention is shown in detail but in an exploded or disassembled view. End portion 40 of second portion 32 (also shown in FIG. 2) has integrally connected thereto a mid-portion 42, through both end portion 40 and mid-portion 42 of which artificial ligament 22 passes. One end 44 of artificial ligament 22 is preferably woven around a loop 46. Loop 46 is connected in a fixed position with respect to male thread 48. Male thread 48 is screwed into female thread 50 located within nose portion 34, as shown in both FIGS. 5 and 6. Male thread 48, loop 46, and artificial ligament 22 (which is woven around loop 46) provide a replaceable loop section 52, which is shown in detail in FIG. 4.

Figure 4A:
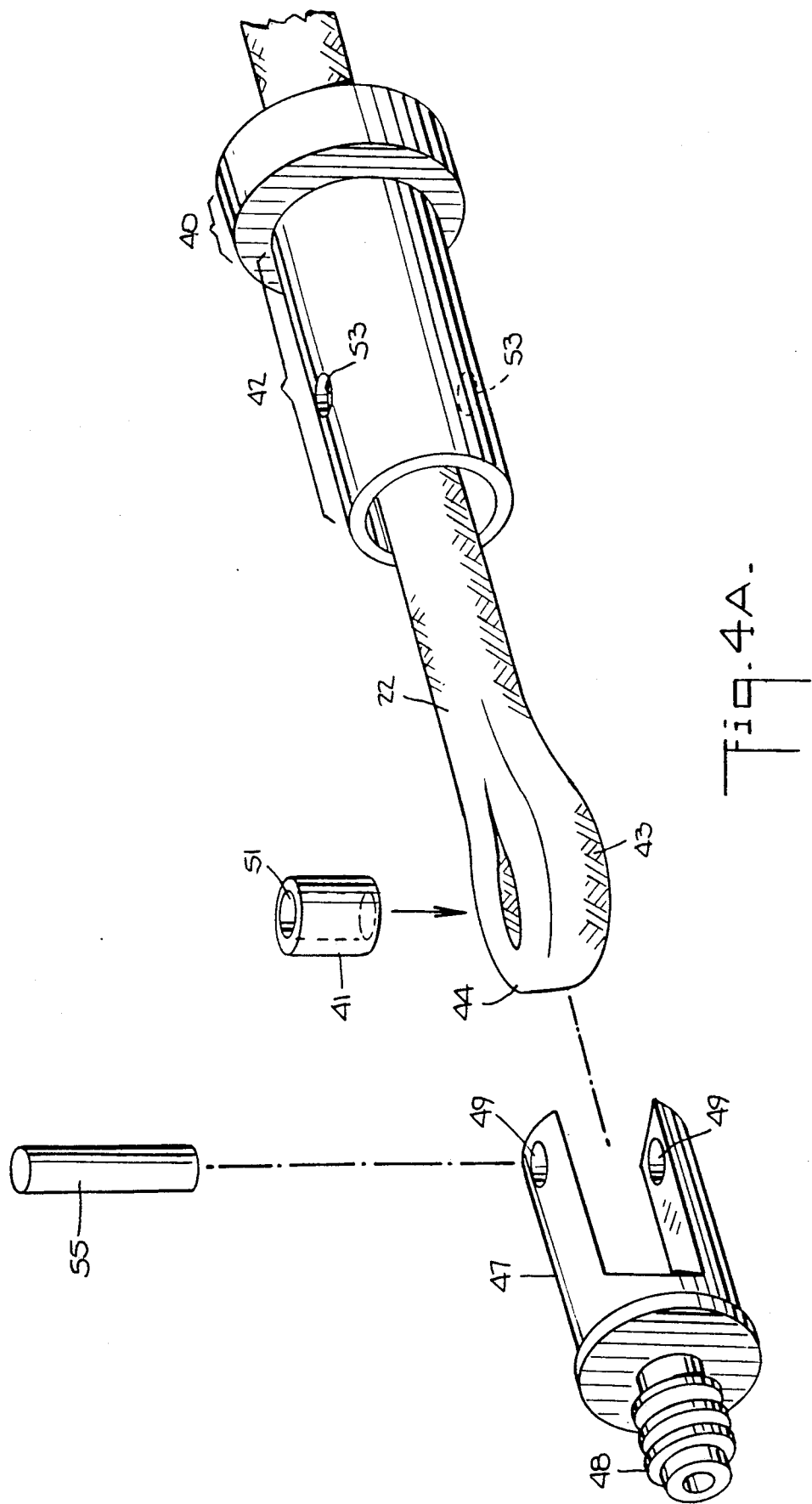
FIG. 4A is an exploded pictorial view of a woven ligament, together with other items which can be assembled together so as to provide a replaceable part.

A preferred way of assembling a woven ligament 22 with other items is described with reference to FIG. 4A. First, obtain a pre-looped woven cord 22, then pass the cord 22 through end-portion 40 and mid-portion 42. Then pass a highly polished cylindrical sleeve 41 through the looped portion 43 of artificial ligament 22 (the diameter of sleeve 41 being only slightly smaller than the diameter of looped portion 43 of ligament 22). Then pass the assembly of sleeve 41 and looped portion 43 into a yoke 47. Next move the mid-portion 42 down along the pre-woven cord 22 and over the yoke 47; and align together the holes 49 in the yoke 47, the hole 51 in the cylindrical sleeve 41, and the hole 53 in mid portion 42, so that a cross-pin 55 can be driven through all of these holes simultaneously, thus creating an assembly of artificial ligament 22 which can be replaced as a unit, if desired.

In FIG. 5, the items described above, especially those in FIGS. 2 and 3, are shown in cross-section. A preferred embodiment of the locking mechanism which is used to lock first portion 30 with second portion 32 is shown in detail in FIGS. 2-12. Preferably, located within first portion 30 in its end portion 31 is a groove 33. This groove has a diameter $d_1$ 35 which is smaller than the diameter $d_2$ 37 of the combination of the two locking pins 54 and spring 56 when spring 56 is in its rest position. Locking pins 54 are interconnected by spring 56 (which is shown in its rest position in FIG. 5 and in its compressed position in FIG. 6). The locking mechanism located within nose portion 34 of second portion 32 is designed to interlock with the locking portion comprising groove 33 having diameter $d_1$ in first portion 30. Thus, the locking mechanism comprises two spring-loaded collapsible pins, which combination has a diameter when the connecting spring is relaxed which is larger than the diameter of groove 33; the pins are adapted to snap into and remain self-locked within groove 33.

However, other suitable locking mechanisms are also within the scope of this invention. For example, alternatively the locking pins 54 could be located, if desired, within first portion 30; and a groove adapted to interlock with those locking pins could alternatively be located within second portion 32.

In FIG. 8, instead of main housing body 38 which is shown in FIGS. 2, 5, and 6 and which is used in the first embodiment of the device of the invention described in FIGS. 1-7 above, a toothed portion 58 is substituted therefor. Toothed portion 58 has individual teeth 60 which clamp into a section of bone in a bone graft 62 (as shown in FIGS. 8-12). The bone graft 62 has a tendon 64 attached thereto, and the bone graft-tendon combination can be originally either from the same individual (i.e., it can be autogenous) or it can be from another individual (i.e., it can be allegraft). The nose portion 34 of the second portion 66 of the second embodiment (described above) is identical to the nose portion 34 of the second portion 32 of the first embodiment, described above. The component parts of second portion 66 are labeled in FIGS. 8–12 so that they correspond to the same parts shown in FIGS. 1–7. The device of the invention can be used to great advantage wherever it is desirable to connect two parts of a joint, either by means of an artificial ligament or by means of a bone graft-tendon connection.

To implant the device of the invention, a suitable method is to drill a hole into bone located on one side of the joint to be repaired, with the diameter of the hole being slightly smaller than that of screw portion 28. The screw portion 28 is then inserted into the drilled hole. After the screw has been inserted into the drilled hole, one then inserts either (1) the mechanical ligament device (which was described above as the first embodiment and which was shown in FIGS. 1–8), to which an artificial ligament is attached or alternatively (2) the second embodiment of the invention which has teeth which are attachable to a bone graft-natural tendon combination. The first and the second portions are then locked together. That self-locking mechanism can be unlocked only by drilling into the device of the invention (preferably through hole 68) so that the spring 56 is destroyed. This unlocking procedure will be done in the event that it is desired to revise the device within the patient, for example, by revising the first embodiment described above to the second embodiment described above, or vice versa.

The device of the invention has many advantages and is useful in a wide variety of types of repairing of joints. The device is revisable from one embodiment to another embodiment, so that two parts of the joint can be joined together either by means of an artificial ligament or by means of a biological graft (either allegraft or autogenous). Such revisions can be very simply done, and this is extremely important when time is of the essence, as is so during surgical operations.

I claim:

1. A device to be placed into one side of a joint, said device comprising:
    (a) a first portion comprising:
        (1) a first screw portion to be screwed into bone in one side of said joint; and
        (2) a first means for locking said first portion; and
    (b) a second portion which is adapted to be inserted during surgery into proximity with and then remain self-locked with said first portion, said second portion comprising:
        (1) a nose portion having a second means for locking said second portion,
    wherein said first means for locking and said second means for locking are adapted to lock together,
    wherein said first means for locking is a groove located either within said first portion or said second portion, and wherein said second means for locking comprises two spring-loaded collapsible pins located either within said second portion or said first portion respectively and which are adapted to snap into and remain self-locked within said groove.

2. A device according to claim 1, wherein said first means for locking is located within said first portion and said second means for locking is located within said second portion and wherein said second portion comprises also:
    (2) a connector portion adapted for connection to an external element.

3. A device according to claim 2, wherein said connector portion adapted for connection to an external element is adapted for connection to an external element selected from the group consisting of (a) bone to natural tendon and (b) artificial ligament.

4. A device according to claim 3, wherein said connector portion comprises a replaceable loop portion comprising an artificial ligament and wherein said loop portion is adapted to fit securely with said nose portion.

5. A device according to claim 4, and including also said artificial ligament.

6. A device according to claim 3, wherein said connector portion comprises a toothed portion having teeth adapted to be inserted into and remain within a bone plug.

7. A device according to claim 3, wherein said device is revisable such that said connector portion can be revised from a replaceable loop portion to a toothed portion or vice versa.

8. A device to be placed into one side of a joint, said device comprising:
    (a) a first portion comprising:
        (1) a first screw portion to be screwed into bone in one side of said joint; and
        (2) a first means for locking said first portion; and
    (b) a second portion which is adapted to be inserted during surgery into proximity with and be snapped together with and then remain self-locked with said first portion, said second portion comprising:
        (1) a nose portion having a second means for locking said second portion,
    wherein said first means for locking and said second means for locking are adapted to snap-lock together,
    wherein said first means for locking is a groove located either within said first portion or said second portion, and wherein said second means for locking comprises at least one spring-loaded collapsible pin located either within said second portion or said first portion respectively and which is adapted to snap into and remain self-locked within said groove.

* * * * *